(12) United States Patent
Alinejad et al.

(10) Patent No.: US 9,028,503 B2
(45) Date of Patent: May 12, 2015

(54) DRILL GUIDE

(75) Inventors: Mona Alinejad, London (GB);
Christopher Alexander Dodd, Oxford (GB); John William Goodfellow, Basingstoke (GB); Russell Lloyd, Wiltshire (GB); David Wycliffe Murray, Oxford (GB); John Joseph O'Connor, Oxford (GB)

(73) Assignees: Biomet UK Limited, Bridgend (GB); Colin Hunsley, Estate of John William Goodfellow, Basingstoke (GB); David Wycliffe Murray, Oxford (GB); Oxford Analysis Ltd., Oxford (GB)

( * ) Notice: Subject to any disclaimer, the term of this patent is extended or adjusted under 35 U.S.C. 154(b) by 224 days.

(21) Appl. No.: 13/510,480

(22) PCT Filed: Nov. 17, 2010

(86) PCT No.: PCT/GB2010/002117
§ 371 (c)(1),
(2), (4) Date: Aug. 30, 2012

(87) PCT Pub. No.: WO2011/061489
PCT Pub. Date: May 26, 2011

(65) Prior Publication Data
US 2012/0323249 A1 Dec. 20, 2012

(30) Foreign Application Priority Data
Nov. 18, 2009 (GB) .................................. 0920225.0

(51) Int. Cl.
A61B 17/60 (2006.01)
A61F 2/00 (2006.01)
A61B 17/17 (2006.01)
A61B 17/72 (2006.01)

(52) U.S. Cl.
CPC ............. *A61B 17/1764* (2013.01); *A61B 17/72* (2013.01)

(58) Field of Classification Search
USPC ........................................... 606/87–90, 96–98
See application file for complete search history.

(56) References Cited

U.S. PATENT DOCUMENTS

| 2,666,430 A | * | 1/1954 | Gispert ............................ 606/96 |
| 2,697,433 A | * | 12/1954 | Zehnder .......................... 606/96 |
| 4,566,448 A | | 1/1986 | Rohr, Jr. |
| 5,314,429 A | | 5/1994 | Goble |
| 5,385,567 A | | 1/1995 | Goble |
| 5,531,751 A | | 7/1996 | Schultheiss et al. |
| 5,669,915 A | * | 9/1997 | Caspar et al. ................... 606/96 |
| 5,911,723 A | * | 6/1999 | Ashby et al. .................... 606/88 |
| 6,702,816 B2 | | 3/2004 | Buhler |
| 7,641,659 B2 | | 1/2010 | Emstad et al. |
| 2006/0064104 A1 | | 3/2006 | Kana et al. |
| 2009/0157077 A1 | | 6/2009 | Larsen et al. |

FOREIGN PATENT DOCUMENTS

| EP | 1095626 A1 | 5/2001 |
| EP | 1479350 A2 | 11/2004 |
| EP | 1709914 A1 | 10/2006 |
| WO | 01/85038 A1 | 11/2001 |
| WO | 03/068119 A2 | 8/2003 |

* cited by examiner

*Primary Examiner* — Anu Ramana
(74) *Attorney, Agent, or Firm* — Harness, Dickey

(57) ABSTRACT

A drill guide comprising: a body comprising a hole extending therethrough for guiding a drill; and an alignment tool, the alignment tool being operable to connect the body to an intramedullary rod, such that the orientation of the body is fixable with respect to the intramedullary rod in an antero-posterior plane and in a transverse plane.

13 Claims, 4 Drawing Sheets

DRILL GUIDE

CROSS-REFERENCE TO RELATED APPLICATIONS

This application is a 371 U.S. National Stage of International Application No. PCT/GB2010/002117, filed Nov. 17, 2010, and published in English as WO 2011/061489 A1 on May 26, 2011. This application claims priority to Great Britain Patent Application No. 0920225.0, filed Nov. 18, 2009. The entire disclosures of the above applications are incorporated by reference herein.

The present invention relates to a drill guide particularly, but not exclusively, a femoral drill guide for use during a partial knee replacement.

BACKGROUND

During knee arthroplasty, particularly a partial knee replacement, the joint is prepared by first resecting the tibial plateau. Following resection of the tibial plateau, one or more holes are then drilled into the femoral condyle to receive a cutting guide for resecting the condyle. Conventionally, a hole is made in the intramedullary canal of the femur, into which an intramedullary rod is inserted. The intramedullary rod acts as a reference for the drilling of the hole or holes which locate the cutting guide. These holes may also serve to locate the femoral component of the prosthetic following resection of the femoral condyle.

The femoral component may comprise a single fixation peg or two fixation pegs which are received in holes in the femur. In addition or as an alternative, the femoral component may comprise one or more webs. The webs may be thin layers of material, which may extend between the pegs.

A two peg component provides greater coverage (i.e. a larger degree of rotation) and may be selected where the patient's lifestyle is such that they are squatting regularly.

As described previously, the intramedullary rod is used as a reference for locating the hole(s) for receiving the cutting guide. A drill guide may be used to reference from the intramedullary rod in order to properly locate the cutting guide. Existing drill guides require the surgeon to align the drill guide with the intramedullary rod in various planes so that the guide hole is placed in the correct position on the femur.

In a known technique, a tibial template is placed on the resected tibial plateau and the drill guide inserted into the operative wound. A feeler gauge is then inserted in between the tibial template and the drill guide. Due to this layering of components there is a stack up in the tolerances of each component.

It is desirable to provide a drill guide which has a simplified alignment process.

STATEMENTS OF INVENTION

According to a first aspect of the invention, there is provided a drill guide comprising: a body comprising a hole extending therethrough for guiding a drill; and an alignment tool, the alignment tool being operable to connect the body to an intramedullary rod, such that the orientation of the body is fixable with respect to the intramedullary rod in an anteroposterior plane and in a transverse plane.

According to a second aspect of the invention, there is provided a drill guide comprising: a body comprising a hole extending therethrough for guiding a drill; wherein the body comprises a fixed foot and a movable foot which are receivable within a joint; wherein the movable foot is releasably attached to the body and, when in a released state, the movable foot is translatable with respect to the fixed foot, such that the fixed foot contacts a first bone of the joint and the movable foot contacts a second bone of the joint.

According to a third aspect of the invention, there is provided a drill guide comprising: a body and a tubular element, the tubular element having a hole extending therethrough for guiding a drill; wherein the tubular element is pivotably mounted with respect to the body such that the angle of the tubular element with respect to the body is adjustable.

Any of the above aspects of the invention may be combined with one or more of the other aspects of the invention and/or one or more of the optional features set out below.

The alignment tool may comprise a first arm and a second arm, the first arm being operable to connect the alignment tool to the body and the second arm being operable to connect the alignment tool to the intramedullary rod.

The first and second arms may be pivotably connected to one another such that the distance between the first and second arms can be altered.

The intramedullary rod may be cannulated and the second arm is received within the intramedullary rod.

The body may have a mounting hole for receiving the alignment tool.

The mounting hole may be angled to the left or right lateral side of the body.

The mounting hole may be angled to the left or right lateral side of the body by 7°.

The mounting hole may be angled in the vertical plane relative to the body.

The mounting hole may be angled down by 5°.

The alignment tool may comprise a handle.

The movable foot may be releasably attached to the body by a screw which passes through a slot in the body and into the movable foot.

The movable foot may be locked in position by tightening the screw such that a section of the body disposed between a head of the screw and the movable foot is held therebetween.

The drill guide may further comprise an incremental locking means for locking the movable foot in predefined positions.

A leading edge of the movable foot may be curved in the plane of the movable foot.

An underside of the movable foot may be curved along its length.

The hole may comprise first and second holes, which extend through the body at different angles.

The first and second holes may be angled at 0° and 10° respectively or 5° and 15° respectively.

The body may further comprise a protrusion on a left lateral side of the body and a protrusion on a right lateral side of the body.

The distance between the protrusions may be equal to a width of a femoral component.

The drill guide may further comprise a locking mechanism for locking the angle of the tubular element with respect to the body.

The drill guide may further comprise an indexing mechanism for positioning the tubular element in predefined angles with respect to the body.

The tubular element may be translatable with respect to the body.

The tubular element may be translatable toward the top or bottom of the body.

BRIEF DESCRIPTION OF THE DRAWINGS

For a better understanding of the present invention, and to show more clearly how it may be carried into effect, reference will now be made, by way of example, to the accompanying drawings, in which.

DETAILED DESCRIPTION

Figure 1:
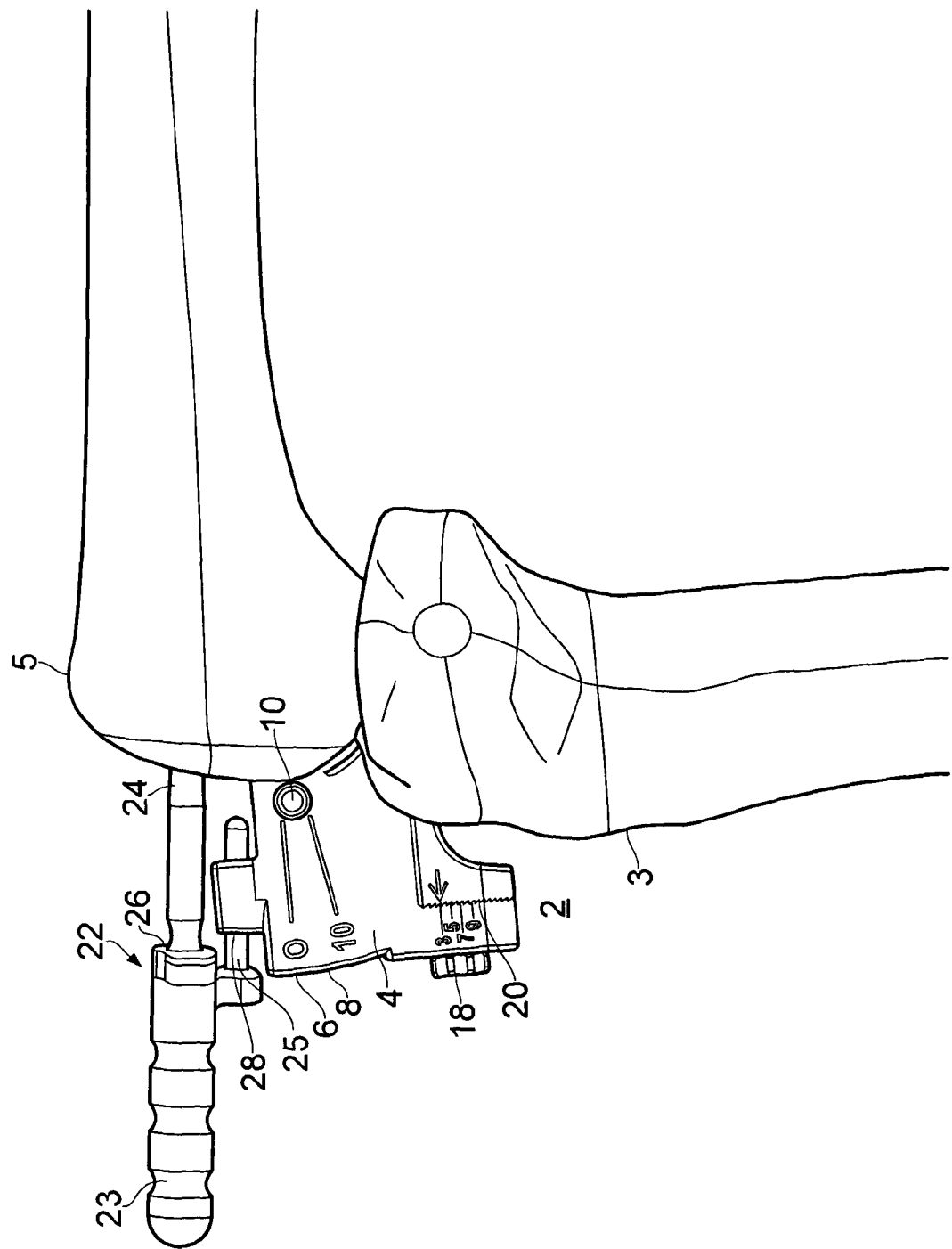
FIG. 1 is a side view of a drill guide in accordance with the invention, wherein the drill guide is in use.
Figure 3:
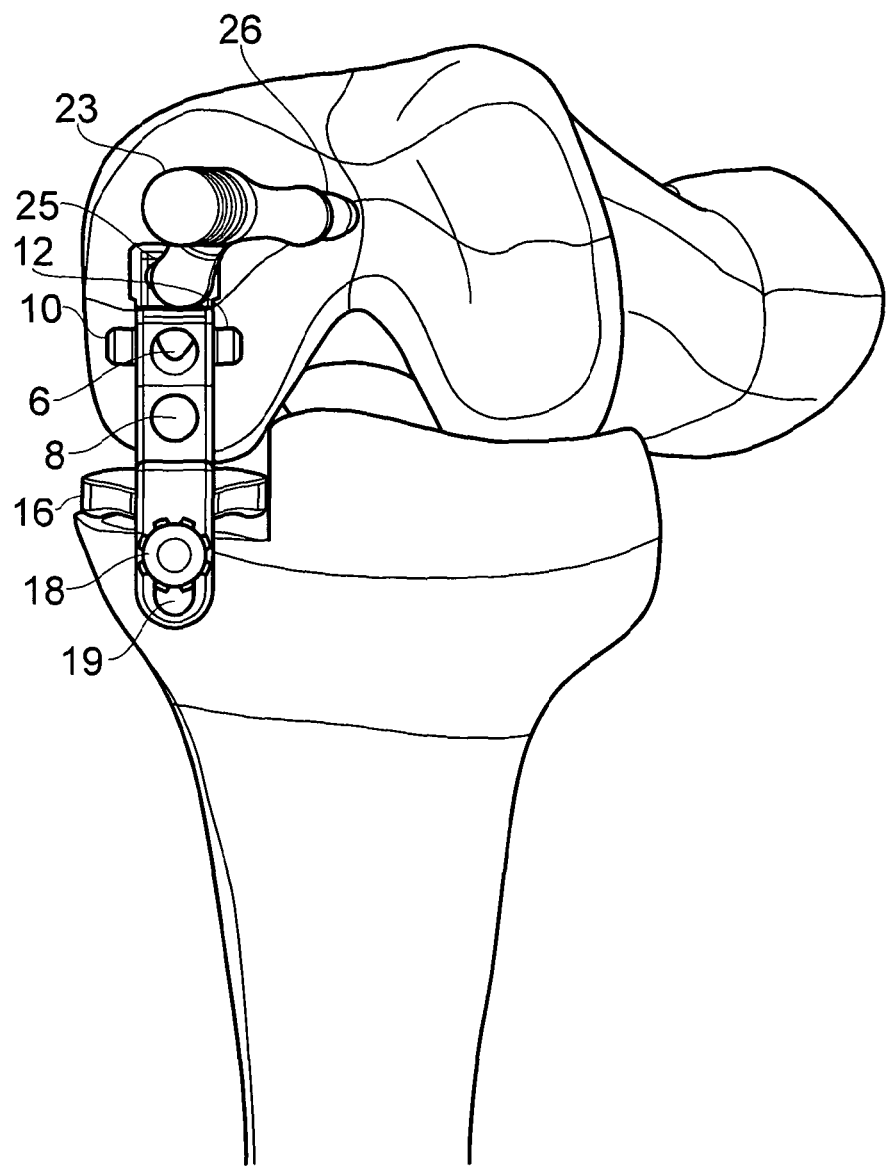
FIG. 3 is a front view of the drill guide.

FIG. 1 shows a drill guide 2 in accordance with a first embodiment of the invention, wherein the drill guide is located in a knee joint between the tibia and the femur. The drill guide 2 comprises a body 4. The body 4 has a first drilling hole 6 and a second drilling hole 8 which each extend longitudinally through the body 4 (as shown in FIG. 3). The first and second drilling holes 6, 8 are aligned at different angles which correspond to the required location of holes for the single peg femoral component or the two peg femoral component. In the Figures, the first and second drilling holes 6, 8 are shown angled at 0° and 10° respectively, however the angles may be chosen as 5° and 15° or other suitable angles for the femoral components which may be used.

The body 4 of the drilling guide 2 is provided with protrusions 10, 12 on both the left lateral and right lateral side of the body 4. The distance from the end of one protrusion to the other is equal to the width of the femoral component and thus provides a means of aligning the drill guide 2 in the centre of the femoral condyle.

The drill guide 2 may be supplied in different sizes which correspond to the size of the femoral component e.g. the width of the component and/or the radius of curvature of the component. Alternatively, the protrusions 10, 12 may be replaced with different sized protrusions to indicate the correct width of the component.

The body 4 is provided with a fixed foot 14 and a movable foot 16. The movable foot 16 is releasably attached to the body 4 by a screw 18 or other such means which passes through a slot 19 in the body 4 and into the movable foot 16. The movable foot 16 is locked in position by tightening the screw 18 such that the section of the body 4 disposed between the head of the screw 18 and the movable foot 16 is held therebetween. The movable foot 16 is released by undoing the screw 18 sufficiently so that the body 4 is no longer held between the head of the screw 18 and the movable foot 16. The movable foot 16 is then free to translate toward or away from the fixed foot 14.

The body 4 and movable foot 16 may be provided with an incremental locking means 20. The incremental locking means 20 allows the movable foot 16 to be translated and locked in predefined positions. The incremental locking means 20 may be provided with a scale for determining the position of the movable foot 16.

The fixed foot 14 is narrow to allow reference off the posterior femoral condyle without interference from femoral osteophytes.

The movable foot 16 has a leading edge which is curved in the plane of the movable foot 16. This allows the movable foot 16 and therefore the drill guide 2 to be angled relative to the vertical cut on the tibial plateau. The underside of the movable foot 16 is also curved along its length. This curvature allows the drill guide 2 to be rotated about the tibial plateau in the anteroposterior plane.

The drill guide 2 further comprises an alignment tool 22 for aligning the body 4. The alignment tool 22 has a handle 23 and a bifurcated end, the bifurcated end having a first arm 25 and a second arm 26. The first arm 25 is received within a mounting hole 28 provided on the top of the body 4 of the drill guide 2. The drill guide 2 is provided with two mounting holes 28 for use of the drill guide 2 on a left or right knee. An intramedullary rod 24 is passed into the intramedullary canal of the patient, which provides a reference for the drill guide 2. At least an end portion of the intramedullary rod 24 is cannulated and the second arm 26 is received within the intramedullary rod 24. Alternatively, the second arm 26 may be cannulated so that the intramedullary rod 24 is received within the second arm 26.

The first and second arms 25, 26 are pivotably mounted on the handle 23 of the alignment tool 22 such that the distance between the first and second arms 25, 26 may be altered.

Figure 2:
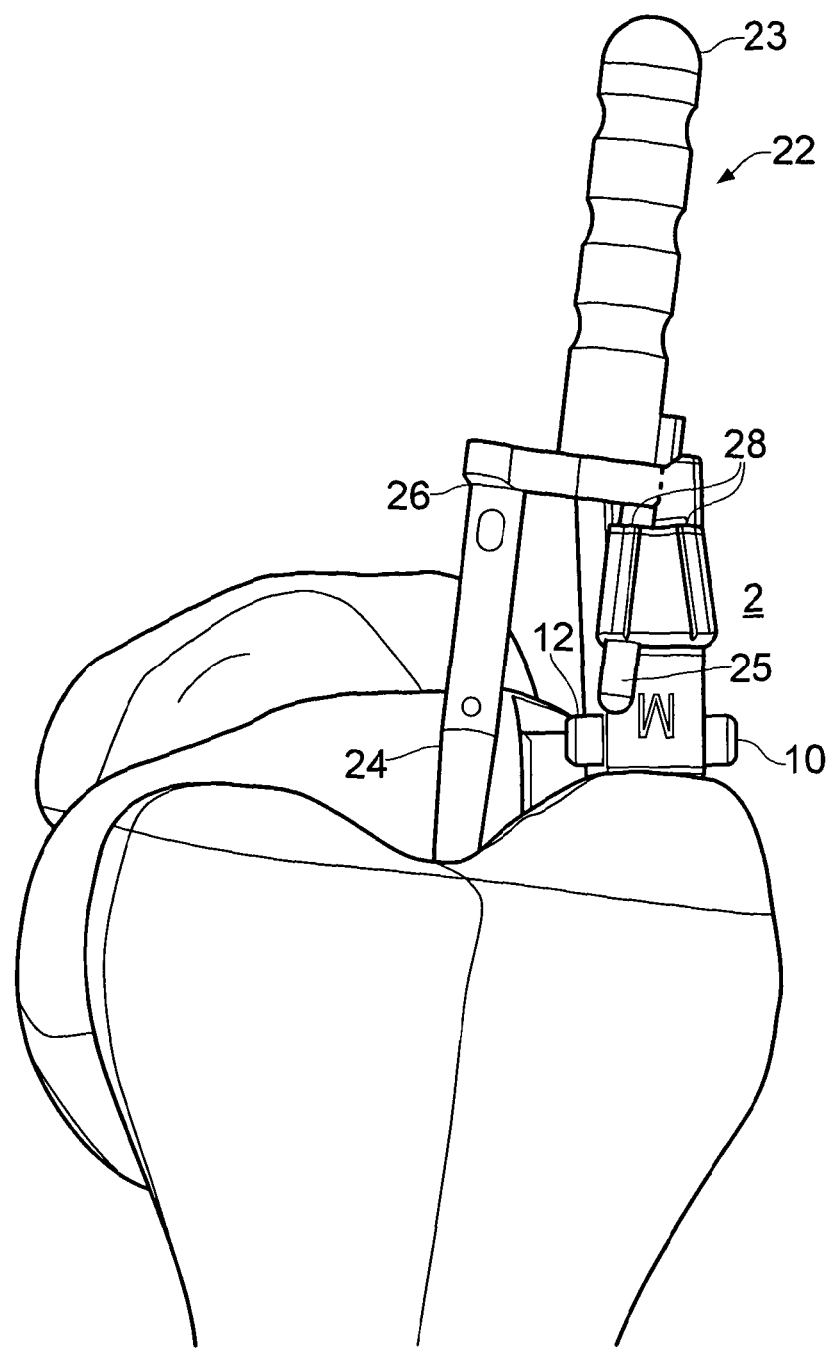
FIG. 2 is a top view of the drill guide.

The mounting holes 28 are angled relative to the body 4, either to the left or right lateral side of the body 4 as shown in FIG. 2, to provide the correct alignment, preferably 7°, for the drill guide 2 relative to the intramedullary rod 24. Also the mounting holes 28 may be angled in the vertical plane relative to the body 4; preferably they are angled down by 5°, as shown in FIG. 2.

In use, following resection of the tibial plateau, the drill guide 2 is inserted into the operative wound of the patient, with the movable foot 16 aligned with the fixed foot 14. The movable foot 16 is then translated vertically such that the fixed foot 14 contacts the posterior femoral condyle and the movable foot 16 contacts the tibial plateau.

The position of the movable foot 16 is determined by the amount of bone resected from the tibial plateau. The scale on the incremental locking means 20 may correspond to a setting on a previously used resection guide. This allows the surgeon to easily adjust the movable foot 16 to the correct position for the amount of bone resected from the tibial plateau so that the drill holes are correctly aligned on the distal femoral condyle.

The alignment tool 22 is connected to both the body 4 and the intramedullary rod 24 by inserting the first arm 25 into the correct mounting hole 28 and by inserting the second arm 26 into the cannulated end of the intramedullary rod 24.

The protrusions 10, 12 on the body 4 are then used to align the drill guide 2 in the centre of the femoral condyle. The pivotably mounted first and second arms 25, 26 allow the distance between the first and second arms 25, 26 to be altered. This allows the drill guide 2 to be moved laterally whilst maintaining the correct alignment with the intramedullary rod 24 in both the anteroposterior and transverse planes.

As mentioned previously, the curvature of the underside of the movable foot 16 allows the drill guide to be rotated about the tibial plateau in the anteroposterior plane. This therefore enables the drill guide 2 to correctly align the drilling holes 6, 8 without the knee being in perfect 90° flexion.

Figure 4:
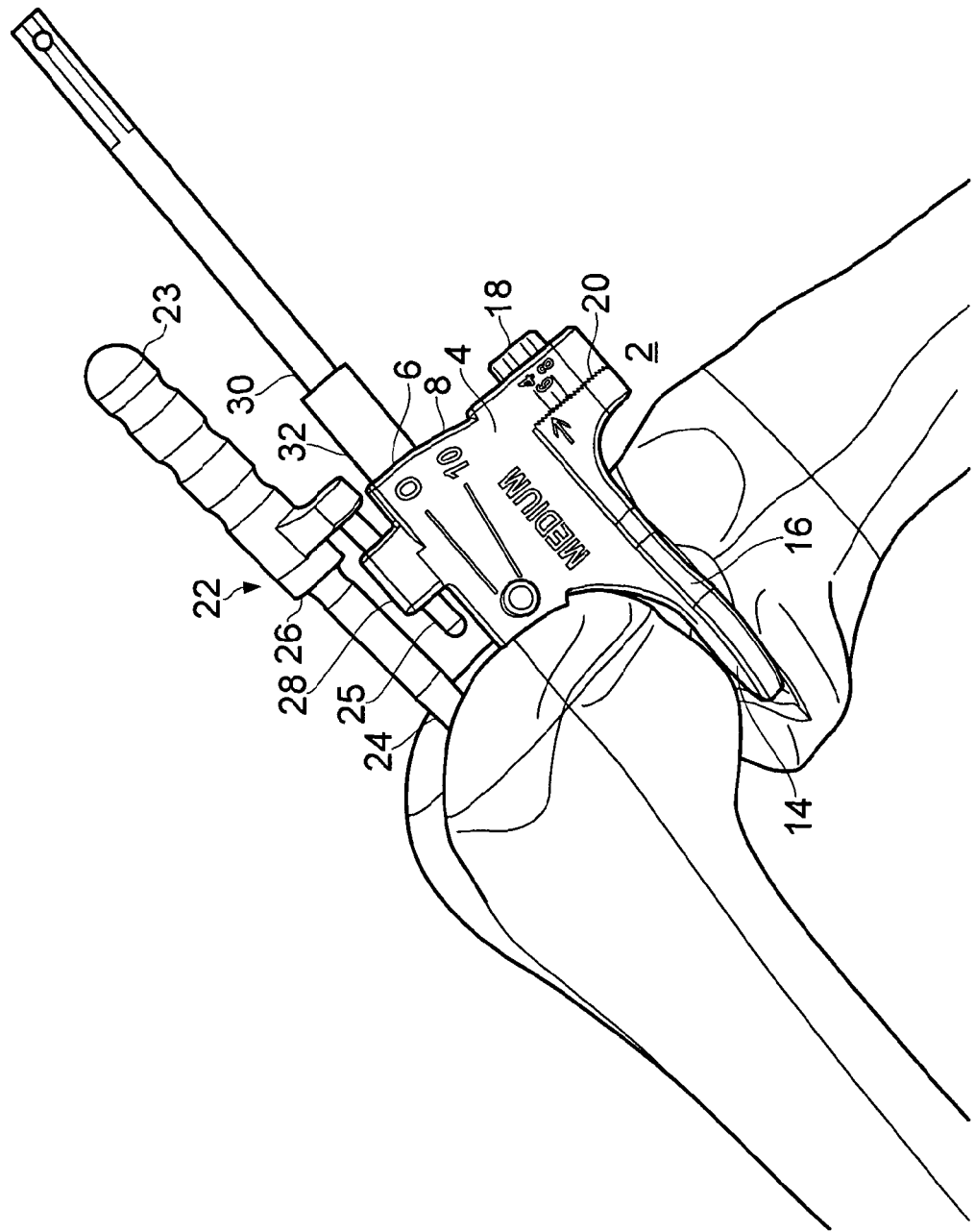
FIG. 4 is a second side view of the drill guide in FIG. 1 during drilling.

As shown in FIG. 4, once the drill guide 2 is correctly aligned a drill 30 is passed through one of the first and second drilling holes 6, 8 and drilled into the distal femoral condyle. The drill 30 is drilled into the distal femoral condyle until a stop 32 on the drill 30 abuts the body 4 and prevents the drill 30 from drilling any deeper. The length of the first and second drilling holes 6, 8 and the length of the drill 30 therefore controls the depth of the hole.

Following drilling, the hole may be used to mount a cutting guide and/or milling spigot for resection of the femoral condyle to the desired shape for the femoral component.

In an alternative embodiment of the invention, the fixed foot may contact the tibial plateau and the movable foot may contact the posterior femoral condyle.

In another embodiment of the invention, the first and second drilling holes 6, 8 may be replaced by a single drilling hole which is pivotably mounted in the body 4. By virtue of this pivotable mounting, the angle of the single drilling hole may be adjusted to correspond to the femoral component and locked in position by a locking mechanism. The locking mechanism and single drilling hole may be provided with an indexing mechanism which provides discrete angles for the single drilling hole.

The present invention has been described in reference to a knee replacement; however the invention may be adapted to be used in other joints.

The present invention provides a drill guide which does not require the use of feeler gauges and which has a direct connection to the intramedullary rod so as to simplify alignment of the drill guide.

The invention claimed is:

1. A drill guide comprising:
   a body comprising a hole extending therethrough for guiding a drill;
   an intramedullary rod; and
   an alignment tool, the alignment tool being operable to connect the body to the intramedullary rod, such that the body is movable laterally relative to the intramedullary rod, while the orientation of the body is fixable with respect to the intramedullary rod in an anteroposterior plane and in a transverse plane;
   wherein the body comprises a fixed foot and a movable foot which are receivable within a joint; and
   wherein the movable foot is releasably attached to the body and, when in a released state, the movable foot is translatable with respect to the fixed foot, such that the fixed foot contacts a first bone of the joint and the movable foot contacts a second bone of the joint.

2. The drill guide as claimed in claim 1, further comprising an incremental locking means for locking the movable foot in predefined positions.

3. A drill guide comprising:
   a body comprising a hole extending therethrough for guiding a drill;
   wherein the body comprises a fixed foot and a movable foot which are receivable within a joint;
   wherein the movable foot is releasably attached to the body and, when in a released state, the movable foot is translatable with respect to the fixed foot, such that the fixed foot contacts a first bone of the joint and the movable foot contacts a second bone of the joint;
   wherein the drill guide further comprises an incremental locking means for locking the movable foot in predefined positions such that the movable foot is not translatable toward or away from the fixed foot;
   wherein the movable foot is releasably attached to the body by a screw which passes through a slot in the body and into the movable foot;
   wherein the movable foot is locked in position by tightening the screw such that a section of the body disposed between a head of the screw and the movable foot is held therebetween.

4. The drill guide as claimed in claim 3, wherein at least one of:
   a leading edge of the movable foot is curved and
   an underside of the movable foot is curved along its length.

5. A drill guide comprising:
   a body comprising a hole extending therethrough for guiding a drill;
   an intramedullary rod; and
   an alignment tool, the alignment tool being operable to connect the body to the intramedullary rod, such that the orientation of the body is fixable with respect to the intramedullary rod in an anteroposterior plane and in a transverse plane;
   wherein the alignment tool comprises a first arm and a second arm, the first arm being operable to connect the alignment tool to the body and the second arm being operable to connect the alignment tool to the intramedullary rod;
   wherein the first and second arms are pivotably connected to one another such that the distance between the first and second arms can be altered.

6. The drill guide as claimed in claim 5, wherein the intramedullary rod is cannulated and the second arm is received within the intramedullary rod.

7. The drill guide as claimed in claim 5, wherein the body has a mounting hole for receiving the alignment tool.

8. The drill guide as claimed in claim 7, wherein the longitudinal axis of the mounting hole is angled in the horizontal plane relative to the body to the left or right lateral side of the body by 7°.

9. The drill guide as claimed in claim 7, wherein the mounting hole is angled in the vertical plane relative to the body by 5° downwards.

10. The drill guide as claimed in claim 5, wherein the alignment tool comprises a handle.

11. The drill guide as claimed in claim 5, wherein the hole is defined by a tubular element which is pivotably mounted with respect to the body such that the angle of the tubular element with respect to the body is adjustable.

12. The drill guide as claimed in claim 5, wherein the hole comprises first and second holes which extend through the body at different angles, of 0° and 10° respectively or 5° and 15° respectively.

13. The drill guide as claimed in claim 5, wherein the body further comprises a protrusion on a left lateral side of the body and a protrusion on a right lateral side of the body, and the distance between the protrusions is equal to a width of a femoral component.

* * * * *